United States Patent
Enggaard et al.

(10) Patent No.: US 9,114,212 B2
(45) Date of Patent: Aug. 25, 2015

(54) AUTO-PRIMING INJECTION DEVICE

(75) Inventors: Christian Peter Enggaard, Vejby (DK); Sara Niemann, Vanlose (DK); Brian Ostergaard, Graested (DK); Jacob Kollerup Jensen, Hellerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 371 days.

(21) Appl. No.: 13/382,413

(22) PCT Filed: Jul. 8, 2010

(86) PCT No.: PCT/EP2010/059824
§ 371 (c)(1),
(2), (4) Date: Mar. 26, 2012

(87) PCT Pub. No.: WO2011/003980
PCT Pub. Date: Jan. 13, 2011

(65) Prior Publication Data
US 2012/0172811 A1    Jul. 5, 2012

Related U.S. Application Data

(60) Provisional application No. 61/224,534, filed on Jul. 10, 2009.

(30) Foreign Application Priority Data

Jul. 8, 2009  (EP) .................................... 09164869

(51) Int. Cl.
| | |
|---|---|
| *A61M 5/315* | (2006.01) |
| *A61M 5/20* | (2006.01) |
| *A61M 5/31* | (2006.01) |
| *A61M 5/24* | (2006.01) |
| *A61M 5/32* | (2006.01) |

(52) U.S. Cl.
CPC .............. *A61M 5/20* (2013.01); *A61M 5/3146* (2013.01); *A61M 5/31578* (2013.01); *A61M 5/24* (2013.01); *A61M 5/3157* (2013.01); *A61M 5/3202* (2013.01); *A61M 2005/2407* (2013.01)

(58) Field of Classification Search
CPC ........... A61M 2005/2407; A61M 2005/31508; A61M 5/24; A61M 5/3146; A61M 5/3157; A61M 3/31578; A61M 5/3202
See application file for complete search history.

(56) References Cited

U.S. PATENT DOCUMENTS

| | | | |
|---|---|---|---|
| 4,592,745 A | * | 6/1986 | Rex et al. ....................... 604/211 |
| 6,514,230 B1 | | 2/2003 | Munk et al. |
| 2011/0046565 A1 | * | 2/2011 | Radmer et al. ................ 604/211 |

FOREIGN PATENT DOCUMENTS

| | | |
|---|---|---|
| EP | 937477 A2 | 8/1999 |
| JP | H11512332 A | 10/1999 |

(Continued)

*Primary Examiner* — Laura Bouchelle
(74) *Attorney, Agent, or Firm* — Wesley Nicolas

(57) ABSTRACT

The invention relates to an injection device (1, 100) configured to perform automatic priming upon removal of a protective cap (15, 115) from a cap receiving portion (9, 109) of a housing (2, 102). When mounted on the injection device (1, 100) the cap (15, 115) defines a first position for a drive member (10, 110) relative to the housing (2, 102), which drive member (10, 110) is capable of causing a piston rod (7, 107) to advance a piston (8, 108) in a reservoir (4, 104). Means (13, 120) are provided defining a second position for the drive member (10, 110) relative to the housing (2, 102). During removal of the cap (15, 115) from the cap receiving portion (9, 109) the drive member (10, 110) moves from the first position to the second position under the influence of a spring (11, 111), thereby causing the piston rod (7, 107) to pressurize the reservoir (4, 104).

10 Claims, 10 Drawing Sheets

(56) References Cited

FOREIGN PATENT DOCUMENTS

| JP | 2003511157 A | 3/2003 |
| WO | 9710865 A1 | 3/1997 |
| WO | 9903520 A1 | 1/1999 |
| WO | 2007066152 A2 | 6/2007 |
| WO | 2009013844 A1 | 1/2009 |
| WO | 2009092807 A1 | 7/2009 |

* cited by examiner

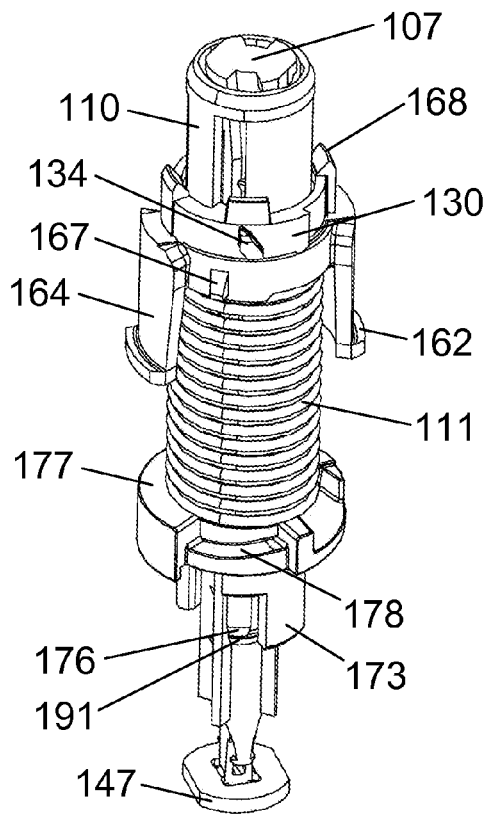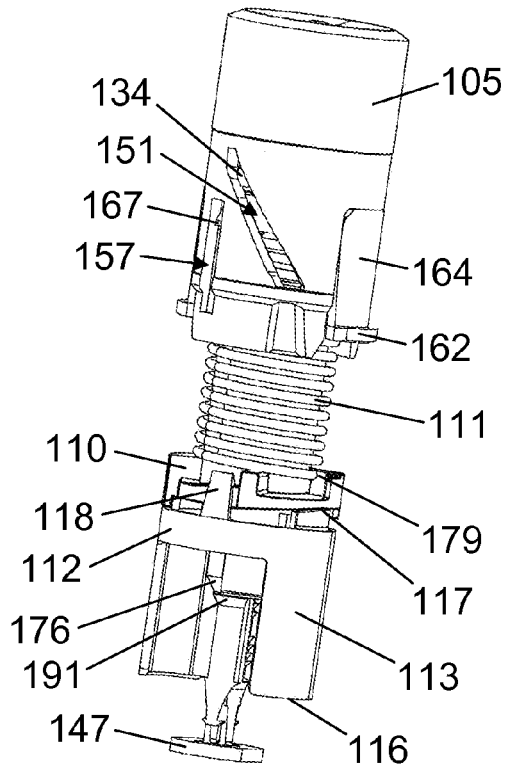
Fig. 16                   Fig. 17
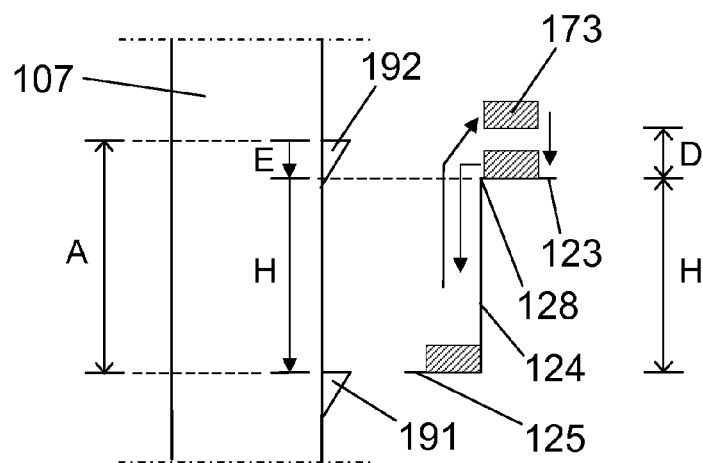
Fig. 18

AUTO-PRIMING INJECTION DEVICE

CROSS-REFERENCE TO RELATED APPLICATIONS

This application is a 35 U.S.C. §371 national stage application of International Patent Application PCT/EP2010/059824 (published as WO 2011/003980), filed Jul. 8, 2010, which claimed priority of European Patent Application EP 09164869.1 filed Jul. 8, 2009; this application further claims priority under 35 U.S.C. §119 of U.S. Provisional Application 61/224,534, filed Jul. 10, 2009.

FIELD OF THE INVENTION

The present invention relates to an injection device for administering a liquid drug. More particularly, the present invention relates to an injection device which does not require separate priming operations by the user. The injection device is particularly suitable for self-injection, e.g. of a glucose regulating drug by a person with diabetes.

BACKGROUND OF THE INVENTION

Within some therapy areas the tendency of a patient to adhere to the prescribed therapy is dependent on the simplicity of the specific treatment regimen. For example, many people with type 2 diabetes are diagnosed with the disease at a relatively high age where they are less prone to accept a treatment that intervenes too much with their normal way of living. Most of these people do not like constantly being reminded of their disease and, as a consequence, they do not want to be entangled in complex treatment patterns or waste time on learning to operate cumbersome delivery systems.

Basically, people with diabetes need to minimise their glucose excursions. Insulin is a well-known glucose lowering agent which must be administered parenterally to be effective in the body. The presently most common way of administering insulin is by subcutaneous injections. Such injections have traditionally been performed using a vial and a syringe, but in recent years so-called injection devices, or injection pens, have gained more and more attention in the marketplace. Many people find these injection devices easier to handle and generally more convenient than the vial and syringe solution. For example, because an injection pen carries a prefilled drug container the user is not required to carry out a separate filling procedure before each injection.

In some prior art injection devices which are suitable for self-injection, the user has to set a desired dose using a dose setting mechanism of the injection device and subsequently inject the previously set dose using an injection mechanism of the injection device. In this case the dose is variable, i.e. the user must set a dose which is suitable in the specific situation each time a dose is to be injected.

Other prior art injection devices are adapted to inject a fixed dose each time it is operated. In this case the user has to prepare the injection device, thereby setting the fixed dose, using a dose setting or dose arming mechanism, and subsequently inject the dose using an injection mechanism.

Regardless of the specific type of injection device it is usually recommended that the user primes the device before an injection to ensure that the amount of drug delivered during the injection actually corresponds to the dose that has been set. For variable dose injection devices priming can be performed by setting a small dose and expelling it outside the body. A piston rod is thereby advanced a small distance in the injection device to cause a piston to pressurise the contents of the container. A small volume of drug is wasted as a result of this action, but the user is then guaranteed both that the piston rod is in operative contact with the piston and that the delivery path has been emptied of air. For fixed dose injection devices, however, such a priming action normally results in wastage of a much larger volume of the drug since the injection device will deliver a specific, therapeutically relevant, dose each time the injection mechanism is activated.

EP 0 937 477 B1 discloses a medication delivery pen which includes a priming control mechanism allowing the user to perform a manual priming by rotating a sleeve about a central part of the pen.

It is desirable to provide an injection device which is simple to handle and which is intuitive and easy for the patient to learn how to use. In particular, it is desirable to provide an injection device which is capable of accurately administering one or more doses of liquid drug, while at the same time requiring a minimum number of operations to be performed by the user. In that respect, it is desirable to provide an injection device which does not require the user to perform a manual priming operation before an injection. Furthermore, specifically in relation to fixed dose injection devices, or other types of injection devices which does not offer user adjustable dose setting, such as e.g. some single shot injectors, it is desirable to avoid wasting a relatively large volume of drug when priming the injection device.

SUMMARY OF THE INVENTION

Various production tolerances in the manufacturing and assembly of prefilled injection pens typically result in slightly varying relative positions of certain internal components of the individual pens. For example, the position of the piston rod relative to the piston in the drug cartridge may vary from pen to pen, i.e. the piston rod does not necessarily abut the piston when the injection pen is supplied from the manufacturer.

Further, in some injection devices, be it prefilled or user filled injection devices, manipulation of the dose setting mechanism may cause a slack between the piston rod and the piston rod drive mechanism, and potentially also between the piston rod and the piston in the container, leaving the piston unsupported with respect to the piston rod and/or the piston rod drive mechanism.

If the user during insertion of an injection needle through the skin accidentally penetrates a blood vessel the blood pressure will force the unsupported piston in the proximal direction and thereby lead to backflow of blood into the container. This situation is undesirable as it may confuse or even frighten the user.

Having regard to the above it is an object of the invention provide an injection device which automatically establishes contact between a movable portion of the drug reservoir and the actuating element that is adapted to reduce the volume of the reservoir when a user readies the device for injection in order to resist a volume expansion of the reservoir in case a blood vessel is penetrated during needle insertion.

It is a further object of the invention to provide an injection device which incorporates an automatic air expelling feature, whereby when a user readies the device for injection air is automatically being removed from the drug delivery path.

In the disclosure of the present invention, aspects and embodiments will be described which will address one or more of the above objects or which will address objects apparent from the below disclosure as well as from the description of exemplary embodiments.

In an aspect of the invention a mechanical injection device for administering a liquid drug is provided, the injection device comprising: a reservoir containing the liquid drug and comprising an outlet and a movable wall, an injection mechanism operable to inject a dose of the liquid drug and comprising force transferring means, e.g. a drive member, an actuation member adapted to cause a displacement of the movable wall, and bias means adapted to provide a force for biasing the force transferring means and/or the actuation member in a direction, a removable cap, and a cap receiving portion adapted to interface with, e.g. to abut or engage with, the cap when the cap is mounted on the injection device, wherein the injection mechanism is operatively coupled with the cap receiving portion and configured to exert a biasing force on the movable wall via the actuation member in response to a relative motion between the cap and the cap receiving portion.

According to the above arrangement a relative motion between the cap and the cap receiving portion will result in the reservoir becoming pressurised. If the reservoir is open to the surroundings, e.g. because a needle assembly is attached to the outlet, thereby penetrating a closure element of the outlet, the biasing force from the actuation member will displace the movable wall and thereby cause a volume of the drug to be expelled from the injection device. If the reservoir is closed the biasing force from the actuation member will keep the reservoir pressurised until e.g. a needle assembly is attached to the outlet, whereafter the movable wall will displace and cause a volume of the drug to be expelled. Either way, such an arrangement provides for an automatic priming of the injection device, and the user does therefore not have to manually perform a separate priming operation before injecting a dose of the drug.

The injection device may further comprise guide means for influencing the motion of one or more parts of the injection mechanism, e.g. the force transferring means and/or the actuation member. For example, the injection device may comprise a guide member adapted to define the maximum possible extent of movement performed by the particular injection mechanism part as a consequence of the relative motion between the cap and the cap receiving portion. Such guide means enables a controlled delivery of an amount of drug which is smaller than the amount expelled following an operation of the injection mechanism, and thereby provides for a priming of the injection device which does not lead to loss of a significant volume of the drug.

In an embodiment of the invention a relative translational motion between the cap and the cap receiving portion causes the actuation member to exert a biasing force on the movable wall.

In an embodiment of the invention a relative rotational motion between the cap and the cap receiving portion causes the actuation member to exert a biasing force on the movable wall.

In an embodiment of the invention a combined relative translational and rotational motion between the cap and the cap receiving portion causes the actuation member to exert a biasing force on the movable wall.

In one embodiment, dismounting the cap from the cap receiving portion causes the actuation member to exert a biasing force on the movable wall.

Dismounting the cap from the cap receiving portion may cause the actuation member to undergo a displacement whereby it is moved into abutment with the movable wall to exert a biasing force on the movable wall. Alternatively, or additionally, dismounting of the cap from the cap receiving portion may cause the actuation member to displace the movable wall.

The injection device may further comprise a housing, e.g. of cylindrical form defining a general longitudinal axis, of a box like form, or of another relevant form. In a specific embodiment of the invention dismounting of the cap from the cap receiving portion causes the actuation member to undergo an axial displacement.

The bias means may comprise geometrical configurations in or of the injection device, energy means, such as a spring, or indeed any means suitable for biasing the force transferring means and/or the actuation member in a certain direction, e.g. towards the reservoir outlet.

The cap may comprise an interface for coupling with the injection mechanism via the cap receiving portion. The interface may be a contact point or surface adapted to abut or engage with a part associated with the injection mechanism, e.g. a part of the injection mechanism itself, such as the force transferring means, or a part coupled with the injection mechanism, such as an intermediate part being coupled with the force transferring means.

The force transferring means may be adapted to act directly on the actuation member or to act on the actuation member via one or more intermediate elements.

In one embodiment of the invention the force transferring means comprises a drive member adapted to cause a movement of the actuation member, and dismounting the cap from the injection device causes the drive member to bring the actuation member into abutment with the movable wall and to thereby pressurise the reservoir.

In another embodiment of the invention the force transferring means comprises a drive member adapted to cause a movement of the actuation member, and dismounting the cap from the injection device causes the drive member to force the actuation member to displace the movable wall.

The force transferring means may comprise a rigid drive member adapted to abut or engage with the actuation member. Alternatively, or additionally, the force transferring means comprises a flexible drive member, such as a spring, adapted to abut or engage with the actuation member or, in case the force transferring means comprises both a rigid and a flexible drive member, with the rigid drive member.

The drive member may be adapted to cause a movement of the actuation member via a ratchet and pawl interface. For example, the actuation member may be toothed and the drive member may comprise an engagement member for interacting with the respective teeth. In this case the actuation member performs a translational movement in response to a translational movement of the drive member, and the guide means is adapted to define a maximum possible extent of translation of the drive member, e.g. to define a translational stop for the movement performed by the drive member in response to a relative motion between the cap and the cap receiving portion.

Alternatively, the drive member may be adapted to cause a movement of the actuation member via a screw thread interface, e.g. comprising a screw thread connection between portions of said two members. The actuation member may be adapted to perform a translational movement in response to a rotational movement of the drive member, e.g. due to the actuation member being in further threaded connection with a housing member or with a separate element which is rotationally locked with respect to the housing. In this case, the guide means is adapted to define a maximum possible extent of rotation of the drive member, e.g. to define a rotational stop for the movement performed by the drive member in response to a relative motion between the cap and the cap receiving portion.

The reservoir may be a rigid container having a movable wall, such as a cartridge comprising an axially displaceable piston. Alternatively, the reservoir may be a flexible container, such as a compressible bag, or a partly rigid and partly flexible container.

In the present context the term 'mechanical injection device' should be interpreted to mean an injection device which is mechanically operated as opposed to electromotor driven injection devices.

In the present context the term 'actuation member' is used to describe the mechanical element that transfers a driving force to the movable wall of the reservoir. The 'actuation member' may comprise a rod and a rod foot, the rod foot being the element physically contacting the movable wall. The rod and the rod foot can be made as two separate pieces or they can be made as one integral element. Alternatively, the 'actuation member' comprises a rod without any foot in which case the rod itself is adapted to physically contact the movable wall. In case the reservoir is a cartridge type reservoir comprising an axially displaceable piston the 'actuation member' may be a piston rod with or without a piston rod foot. It is noted that the term 'actuation member' also encompasses other suitable structures for transferring a driving force to the movable wall, such as e.g. a plate or a diaphragm.

In the present context the term 'liquid drug' should be interpreted to mean a drug in a liquid state, such as, e.g., a solution or a suspension.

The injection device may be of the kind which is able to deliver only a single dose of the drug. Alternatively, the injection device may be of the kind which is able to repeatedly set and deliver a dose of the drug. In that case, the injection device further comprises dose setting means operable to set a dose. In a specific embodiment, the injection device is able to repeatedly set and deliver a predetermined dose.

In the present context the term 'predetermined dose' should be interpreted in such a manner that when the dose setting means is operated a specific fixed dose is set, i.e. it is not possible to set an arbitrary dose. However, the predetermined dose may be variable in the sense that it may be possible to initially set the injection device to a selected dose, and the dose setting means will then set this selected dose each time the dose setting means is operated.

The dose setting means, or dose arming means, is the part of the injection device which is operated when a dose is being set. The dose setting means comprises a mechanism which brings elements of the injection device into such relative positions that a given amount of drug will be delivered upon operation of the injection mechanism. The injection mechanism is the part of the injection device which, when operated, is causing a set dose to be injected. The injection mechanism comprises a force transferring element, e.g. a movable actuation member, being adapted to cooperate with the movable wall, e.g. a piston, of the reservoir in such a manner that operation of the injection mechanism causes the actuation member to move whereby the piston is moved inside the reservoir in a direction which causes liquid drug to be expelled from the reservoir, e.g. via a needle in a needle assembly attached thereto. The dose setting mechanism and the injection mechanism may share one or more structural and/or functional elements.

The removable cap may be adapted to cover an outlet portion of the injection device, such as a needle holding portion or a jet injection nozzle, when the injection device is not in use. Thereby the removable cap is capable of e.g. protecting a needle mounted on the needle holding portion, preventing needle sticks and/or preventing accidental spilling of liquid drug. The cap can be removed, uncovering the outlet portion, when it is desired to inject a dose of the drug.

The cap receiving portion is a portion of the injection device which is adapted to receive and hold the removable cap when it is mounted on the injection device. It may comprise means for retaining the cap, such as a bayonet joint, a threaded portion, a snap lock, etc. The cap receiving portion may be adapted to receive the cap when the cap is mounted on the injection device to cover the distal, or outlet, portion of the injection device. Alternatively, the cap receiving portion may be adapted to receive the cap when the cap is mounted on the proximal portion of the injection device. If the cap receiving portion is adapted to receive the cap when the cap is mounted on the injection device to cover the outlet portion thereof, and/or of the reservoir, the above described automatic priming function will even become a part of a natural or well-known use pattern since a medical injection device conventionally requires a user to remove a protective cap from its outlet portion in order to be able to perform an injection. In other words, the priming is performed automatically by the injection device without the user having to learn and carry out any additional operation steps.

The interface between the cap and the cap receiving portion may be such that the cap is dismounted from the cap receiving portion in a substantially linear movement, in a rotational movement, e.g. a purely rotational or a spiralling movement, or in a combination of a linear and a rotational movement.

The dose setting means may be operatively coupled to the cap receiving portion, i.e. performing specific operations of the cap receiving portion affects the dose setting means. More particularly, the dose setting means and the cap receiving portion may be coupled in such a manner that mounting of the cap on the injection device causes the dose setting means to set a dose. The dose setting means and the cap receiving portion may be mechanically coupled, either directly or via one or more intermediate parts, or they may be coupled in any other suitable way as long as specific operations of the cap receiving portion affects the dose setting means in such a manner that the dose is set.

In a particular embodiment of the invention, mounting the cap on the injection device causes an element to move axially with respect to the actuation member to thereby move an engagement member along the actuation member to a more proximal position. Each time the cap is mounted on the injection device the engagement member is thus moved further along the actuation member towards the proximal end thereof.

The bias means may comprise energy means acting to release stored energy during injection of a dose of drug, the released energy causing the dose to be injected. The energy means may be connected to the dose setting means in such a manner that energy is stored in the energy means during setting of a dose.

The energy means may comprise a spring member which may be adapted to be loaded along its centre axis, e.g. by compressing the spring or elongating the spring. The spring member may be a compressible spring or a torsion spring. In the case that the spring member is a compressible spring, the injection device may for example be operated in the following manner. When the cap is mounted on the cap receiving portion a spring compressing element is moved, e.g. in an axial direction, thereby compressing the spring. The spring compressing element is locked in this position, thereby retaining the spring member in the compressed state. Dismounting the cap from the cap receiving portion will unlock the spring compressing element and cause the spring to displace the spring compressing element a small distance axially and urge the spring compressing element into abutment or engagement with a retention structure that retains it from further axial movement. The small axial displacement of the spring compressing element will cause an axial movement of the actuation member, due to an engagement between the spring compressing element and the actuation member being effectuated by the movement of the spring compressing element. This will force the actuation member into abutment with the movable wall and pressurise the reservoir. In case the reservoir outlet is open, e.g. if an injection needle is attached thereto, this will result in a small volume of drug being expelled from the reservoir. When the injection needle has subsequently been inserted at a desired injection site, the injection button is pressed. This causes the spring compressing element to be moved out of engagement with the retention structure, and the energy stored in the spring is thereby released in such a manner that it causes the actuation member to move while displacing the movable wall, thereby causing a dose of drug to be injected from the reservoir, via the injection needle.

In an arrangement as the above described when the user removes the cap from the injection device the actuation member automatically undergoes an axial displacement to secure an abutment with the movable wall. This eliminates any slack in the injection system that may have been introduced at an earlier stage of use. If the reservoir outlet is open, e.g. if an injection needle is attached to the injection device, it will also result in a small volume of drug being expelled from the reservoir through the injection needle. The user does therefore not have to perform a separate action to ensure that any potential residual air is removed from the drug delivery line. By simply removing the cap from the injection device the user automatically readies the injection device for injection of a precise amount of drug. Notably without having wasted a large volume of drug for the priming of the injection device.

In an exemplary embodiment, the drive member is adapted to undergo relative motion with respect to the actuation member during dose setting and to transmit a driving force to the actuation member during dose injection. The drive member may be coupled with the energy means in such a manner that movement of the drive member causes the energy means to store and/or release energy and, conversely, in such a manner that release of energy from the energy means causes the drive member to move. The energy means may in that respect comprise a compression spring which is rotationally pre-stressed to bias the drive member in both a specific translational direction and a specific rotational direction. The drive member may therefore also serve as a spring compressing element. Alternatively, the energy means may comprise other arrangements capable of storing and releasing energy for translational and rotational motion, such as for example two or more springs each being able to provide a share of the energy needed for translational and rotational motion, e.g. a compression spring capable of providing energy for translational motion and a torsion spring capable of providing energy for rotational motion, an axially compressible torsion rod or an arrangement comprising a rotationally pre-stressed tension spring.

The actuation member may comprise a set of axially spaced apart teeth for engagement with one or more engagement elements, and the drive member may comprise an engagement element adapted to engage with the actuation member teeth. In such an embodiment, when the dose setting means is operated to set a dose the drive member will undergo relative motion with respect to the actuation member whereby the engagement element will be moved out of engagement with a tooth on the actuation member and moved along the actuation member to pass a more proximally positioned tooth. When the injection mechanism is subsequently operated to inject the set dose the engagement member will engage the tooth it just passed and the drive member will move distally in the housing while slaving the actuation member.

Guide means may be provided for guiding the movement of the drive member and/or the actuation member. The guide means may form part of the housing or may comprise a separate element having a fixed position relative to the housing. Alternatively, or additionally, the guide means may comprise an element capable of moving relative to the housing. The guide means may be configured to enable the drive member and the actuation member to perform a purely translational relative motion during one part of the relative motion and to perform a combined translational and rotational relative motion during another part of the relative motion. The guide means may comprise a first resting surface, or first retention plateau, for supporting the drive member in a well-defined axial position, and a second resting surface, or second retention plateau, for supporting the drive member in another well-defined axial position. In one particular embodiment the axial distance between the first retention plateau and the second retention plateau corresponds to the axial displacement of the drive member during an injection.

In one embodiment of the invention the actuation member comprises two or more spaced apart teeth adapted to be engaged by the drive member, the distance between two consecutive teeth being greater than the axial distance between the first retention plateau and the second retention.

In an exemplary embodiment of the invention the guide means comprise a first guide member fixedly arranged in the housing and a second guide member movably arranged in the housing. The first guide member comprises a longitudinal first guiding surface which is substantially parallel with the actuation member and which enables the purely translational relative motion between the drive member and the actuation member. The second guide member comprises a sloping second guiding surface which enables the combined translational and rotational relative motion between the drive member and the actuation member.

In another embodiment of the invention the guide means comprise a first guide member fixedly arranged in the housing and a second guide member arranged on the removable cap. The first guide member comprises a longitudinal first guiding surface which is substantially parallel with the actuation member and which enables the purely translational relative motion between the drive member and the actuation member. The second guide member comprises a sloping second guiding surface which enables the combined translational and rotational relative motion between the drive member and the actuation member.

In a specific embodiment of the invention the cap comprises a round-going edge capable of transferring a force to the drive member, or to an intermediate element being coupled with the drive member, such that when the cap is mounted on the injection device at the cap receiving portion the drive member is forced to take up a certain position with respect to the cap receiving portion in which the drive member is out of engagement with the actuation member. As long as the cap is mounted on the injection device the drive member is held in this position against the biasing force of the bias means. When the cap is dismounted from the cap receiving portion the drive member is forced to undergo a displacement towards the movable wall due to the biasing force of the bias means. This displacement is predetermined by the initial distance between the cap edge when the cap is mounted on the cap receiving portion and the first retention plateau.

During the displacement the drive member engages with the actuation member and exerts a force on the actuation member towards the movable wall. If there is a slack between the actuation member and the movable wall the actuation member will be slaved into abutment with the movable wall. Then, if the reservoir outlet is closed the actuation member will pressurise the reservoir. However, if the reservoir outlet is open the movement of the actuation member will cause the movable wall to displace a small distance, thereby reducing the volume of the reservoir.

In case the actuation member comprises a piston rod and a piston rod foot these may be physically joined, e.g. welded or glued together, by the manufacturer. Particularly, when the piston rod foot and the piston rod are joined the piston rod foot may be in contact with the movable wall, and the drive member may be lifted to a position just proximally of, e.g. 0.5-1 mm above, the first retention plateau, whereby when the joining is completed and the drive member is released the bias means will apply a distally directed force on the drive member, which in turn applies a distally directed force on the piston rod, resulting in the reservoir becoming pressurised. This means that when e.g. an injection needle assembly is attached to the outlet in connection with a first use of the injection device the excess pressure in the reservoir is relieved and the drive member is moved to the first retention plateau by the bias means while slaving the piston rod a small distance, leading to a priming volume of drug being expelled through the needle. Importantly, during the joining of the piston rod and the piston rod foot the drive member is not lifted any further than it is moved by the cap when the cap is mounted on the injection device. This is to avoid a situation where the reservoir is under pressure during long term storage of the injection device.

When stored for some time an injection device which employs a cartridge type glass reservoir comprising a displaceable rubber piston may experience a problem of the piston sticking to the cartridge wall. This may lead to uncontrolled piston movement during dose delivery. If the injection system is pre-compressed according to the above sufficient pressure will be available to start the movement of the piston in the cartridge once the injection device is used for the first time, and dose accuracy is thereby assured.

In another aspect of the invention a method for priming an injection device is provided, the method comprising:
    providing an injection device, comprising: a variable volume reservoir containing an amount of drug and comprising an outlet and a movable wall, an actuation mechanism operable to cause movement of the movable wall, and a removable cap adapted to couple with the actuation mechanism via a cap receiving portion when the cap is mounted on the injection device, and
    introducing a relative motion between the cap and the cap receiving portion.

In one embodiment thereof the method comprises:
    providing an injection device, comprising: a variable volume reservoir containing an amount of drug and comprising an outlet and a movable wall, an actuation mechanism operable to cause movement of the movable wall, a removable cap, and a cap receiving portion adapted to abut or engage with the cap when the cap is mounted on the injection device, the cap receiving portion and the actuation mechanism being coupled such that mounting of the cap on, and dismounting of the cap from, the cap receiving portion affects the position of the actuation mechanism, and
    dismounting the cap from the injection device.

The reservoir may further comprise an outlet closure, e.g. a pierceable septum or the like, adapted to prevent leakage of drug from the injection device during non-use periods. In that case the method further comprises penetrating the outlet closure with a pointed object to establish fluid connection between the outlet and the exterior of the reservoir. In a particular embodiment the method further comprises mounting an injection needle assembly comprising a double-pointed injection needle onto the injection device to penetrate the outlet closure.

In another embodiment, a method for priming a medical injection device is provided, the method comprising:
    providing an injection device, comprising: a variable volume reservoir containing an amount of drug and comprising an outlet and a movable wall, an actuation mechanism operable to cause movement of the movable wall, a removable cap, and a cap receiving portion adapted to abut or engage with the cap when the cap is mounted on the injection device and to provide a coupling region for coupling of the cap and the actuation mechanism, and
    introducing a relative motion between the cap and the cap receiving portion.

In a specific embodiment, the above method comprises performing an action to introduce a relative translatory motion between the cap and the cap receiving portion.

By any of the above described methods, which are carried out before fluid communication is established between the reservoir and the target compartment in the body of the subject user, the injection device is guaranteed to get rid of a potential slack in the actuation mechanism and is thereby readied for subsequent precise delivery of the drug.

In injection devices not employing energy means, such as a spring, for causing an automatic ejection of the drug from the reservoir the user himself applies the force necessary to drive the actuation member. This implies that if the injection is for some reason obstructed, e.g. due to clogging, the user will know instantly because he will suddenly need to apply an increased push force to the injection button to overcome the resistance in the system.

In injection devices which offer automatic injection, however, there is a risk that an obstruction to the delivery is not detected by the user since he is not directly involved in the actuation of the piston. For example, the user may push the injection button to thereby release a spring which then forces the piston to move in the reservoir. If the delivery path is somehow obstructed the spring may not be sufficiently powerful to overcome the resistance in the system, resulting in an incomplete dose being delivered. The user may not sense the obstruction and think that he has received the entire dose. Such a situation could have dangerous consequences.

It is therefore desirable to provide an automatic injection device which is able to inform the user that an injection has been completed.

Thus, in yet another aspect of the invention an automatic injection device is provided, comprising: a housing comprising a window, a variable volume reservoir containing a drug, and an injection mechanism operable to inject a dose of the drug, the injection mechanism comprising an actuation member and bias means for causing a displacement of the actuation member from a first position in which a dose is set to a second position in which the set dose has been delivered from the reservoir, wherein the window displays a first combination of colours when the actuation member is in the first position and a second combination of colours when the actuation member is in the second position.

In the present context, a combination of colours may be a combination of two or more colours or it may simply be a single colour. In an exemplary embodiment of the invention a first colour is displayed in the window when the actuation member is in the first position and a second colour is displayed when the actuation member is in the second position, the second colour being visually distinct from the first colour, i.e. the reflectivity of the material part displayed in the window when the actuation member is in the first position and the reflectivity of the material part displayed in the window when the actuation member is in the second position are different to visible light rays.

By such an arrangement the user is able to check if the injection is complete by checking if the second colour has appeared in the window. In a specific embodiment of the invention when the second colour fills up the whole window the injection is complete.

In the present specification reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in at least that one aspect or embodiment of the invention, but not necessarily in all aspects or embodiments of the invention. It is emphasized, however, that any combination of features, structures and/or characteristics described in relation to the various aspects and embodiments of the invention is encompassed by the invention unless otherwise indicated herein or clearly contradicted by context.

The use of any and all examples, or exemplary language (e.g., such as, etc.), in the text is intended merely to illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein FIG. 16 is a perspective view of parts of an injection mechanism, showing a relation between the drive member, the piston rod, the spring, the spring holding element and the coupling element, FIG. 17 is a perspective view of the injection mechanism of FIG. 16, including the injection button and the push element, FIG. 18 is a two-dimensional representation of the movement of the drive member during dose setting, respectively injection.

In the figures like structures are mainly identified by like reference numerals.

DESCRIPTION OF EXEMPLARY EMBODIMENTS

When in the following relative expressions, such as "clockwise" and "counter-clockwise" and "proximally" and "distally", are used, these refer to the appended figures and not necessarily to an actual situation of use. The shown figures are schematic representations for which reason the configuration of the different structures as well as their relative dimensions are intended to serve illustrative purposes only.

Figure 1:
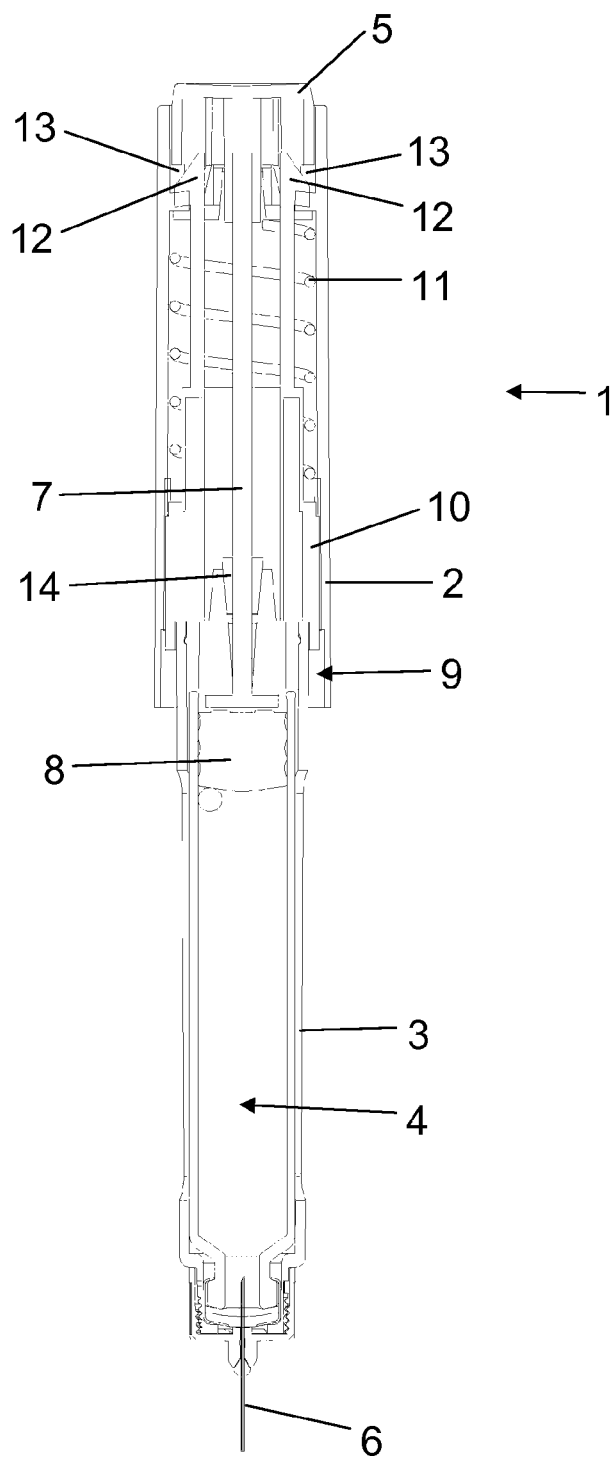
FIG. 1 is a cross sectional view of an injection device according to a first embodiment of the invention in an unloaded state.

FIG. 1 is a cross sectional view of an injection device 1 according to a first embodiment of the invention. In FIG. 1 the injection device 1 is shown in an unloaded state, i.e. a dose has not yet been set.

The injection device 1 comprises a housing 2, a cartridge holding part 3 having a cartridge 4 arranged therein, and an injection button 5. At a distal end of the cartridge holding part 3 an injection needle 6 is attached. A piston rod 7 is arranged in abutment with a piston 8 arranged in an interior part of the cartridge 3 in such a manner that moving the piston rod 7 in a distal direction will cause the piston 8 to move in a distal direction, thereby causing liquid drug from the cartridge 4 to be expelled via the injection needle 6.

When a user has completed an injection a cap (not shown in FIG. 1) is mounted on the injection device 1 at a cap receiving portion 9 in such a manner that the injection needle 6 is covered. When the cap is mounted at the cap receiving portion 9 it pushes against a driver 10, thereby moving it in a proximal direction. This causes a spring 11 to be compressed, thereby storing energy in the spring 11, and moves a couple of snap arms 12 in a proximal direction to a position beyond protrusions 13 arranged in the housing 2.

The driver 10 is connected to the piston rod 7 via teeth (not shown) formed on the piston rod 7 and a tooth engaging part 14 formed on the slider 10. The teeth and the tooth engaging part 14 are arranged in such a manner that the tooth engaging part 14 is allowed to pass over the teeth when the driver 10 is moved in a proximal direction relative to the piston rod 7, but the piston rod 7 must move along with the driver 10 when the driver 10 is moved in a reverse direction.

Furthermore, the movement of the driver 10 in a proximal direction as described above causes the injection button 5 to be moved in a proximal direction, i.e. it causes the injection button 5 to protrude from the housing 2, thereby indicating to a user that the injection device 1 has been loaded.

Figure 2:
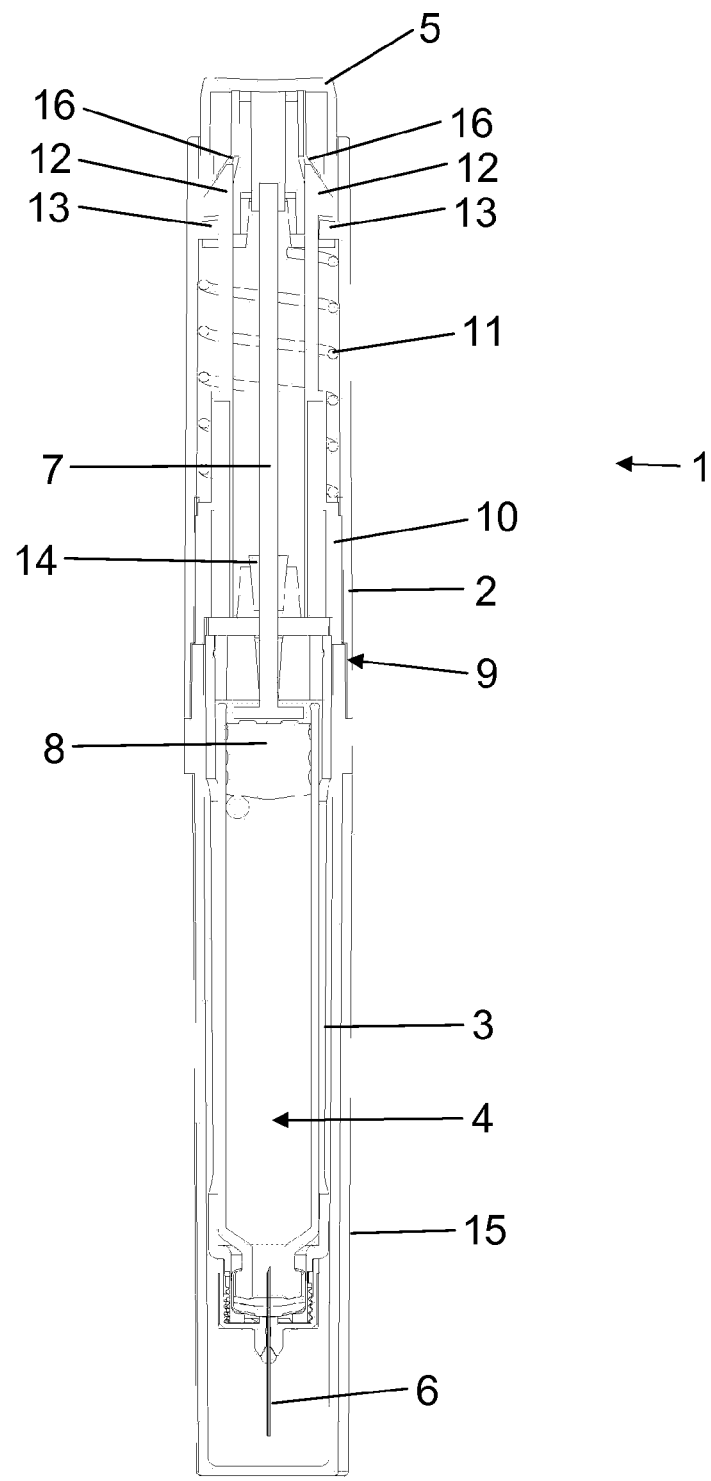
FIG. 2 is a cross sectional view of the injection device of FIG. 1 in a loaded state.

FIG. 2 is a cross sectional view of the injection device 1 of FIG. 1 in a loaded state. In FIG. 2 a cap 15 has been mounted on the injection device 1 at the cap receiving portion 9. It is clear that the injection button 5 has been moved in a proximal direction as compared to the position shown in FIG. 1. It is also clear that the snap arms 12 have been moved in a proximal direction beyond the protrusions 13.

The injection device 1 is designed such that when the cap 15 is mounted at the cap receiving portion 9 the snap arms 12 are moved a distance proximally beyond the protrusions 13 (not visible in FIG. 2), i.e. the snap arms 12 are not in engagement with the protrusions 13. As long as the cap 15 is mounted on the injection device 1 the contact interface between the cap 15 and the driver 10 is in effect retaining the spring 11 in the compressed state. When the cap 15 is dismounted from the cap receiving portion 9 the spring 11 releases some of its stored energy and forces the driver 10 in the distal direction until the snap arms 12 engage with the protrusions 13. At this point the protrusions 13 will retain the spring 11 in a new, slightly less compressed state.

During the motion of the driver 10 whereby the snap arms 12 are moved into engagement with the protrusions 13 the tooth engaging part 14 engages a tooth (not shown) on the piston rod 7 and displaces the piston rod 7 a small distance distally. This displacement of the piston rod 7 is transferred to the piston 8, leading to a small volume of drug being expelled from the reservoir 4 through the needle 6.

When it is desired to inject the set dose, the user inserts the injection needle 6 at a suitable injection site. The injection button 5 is then pushed in a distal direction, i.e. towards the housing 2 and the position shown in FIG. 1. This causes pushing surfaces 16 to push snap arms 12 towards the centre of the injection device 1, thereby releasing them from the protrusions 13. Accordingly, the driver 10 is allowed to move in a distal direction, and the energy stored in the spring 11 during setting of the dose will cause this movement to take place. Due to the engagement between the teeth of the piston rod 7 and the teeth engaging part 14 of the driver 10, the piston rod 7 is moved along. Thereby the piston 8 is also moved in a distal direction, causing the dose to be expelled from the cartridge 4 via the injection needle 6.

When the injection has been completed, the cap 15 is once again mounted on the injection device 1 at the cap receiving part 9, thereby causing a new dose to be set as described above. Since the driver 10 is moved the same distance each time the cap 15 is mounted on the injection device 1, the set dose is a predetermined, fixed dose.

Figure 3:
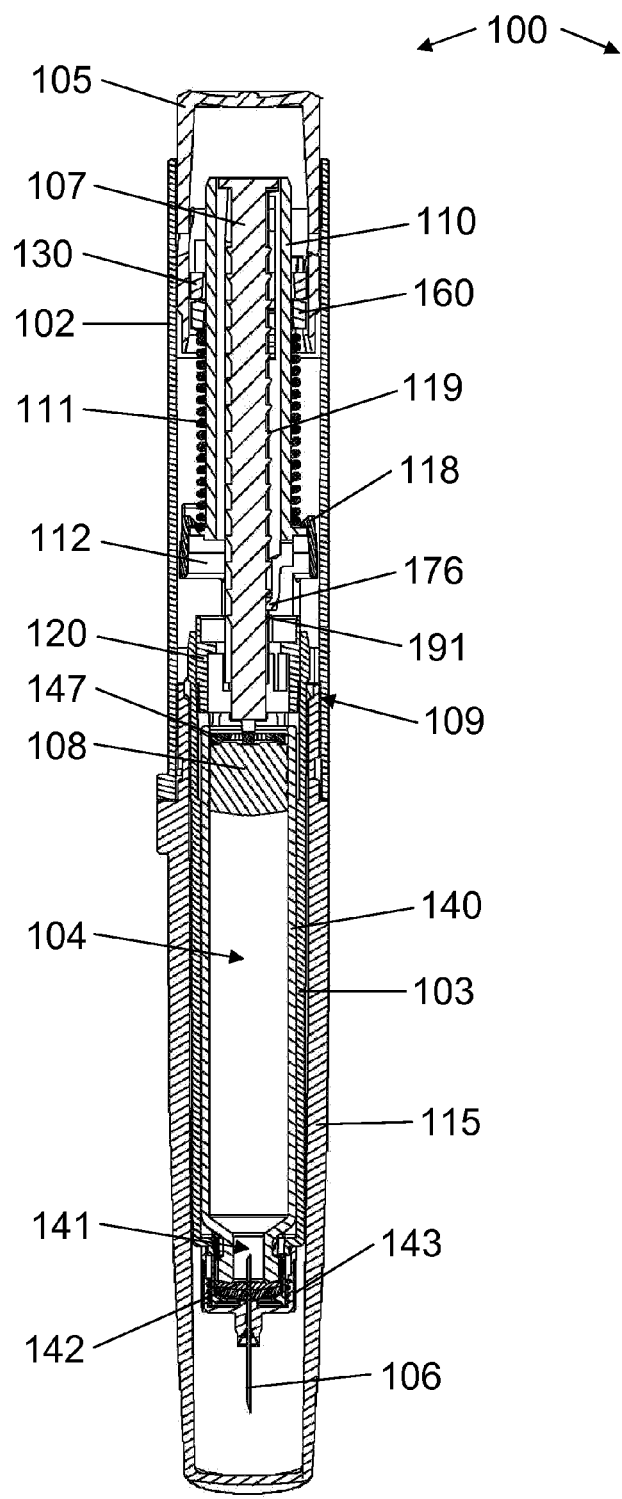
FIG. 3 is a cross sectional view of an injection device according to a second embodiment of the invention before the first injection.

FIG. 3 shows an injection device 100 according to a second embodiment of the invention. The injection device 100 is in a loaded state as delivered from the manufacturer, i.e. it has not yet been used for injection. The injection device 100 comprises a housing 102 and a cartridge holding part 103 for supporting a cartridge 104 which contains the liquid drug. The liquid drug is positioned between a piston 108, which is capable of moving axially in the cartridge 104, a tubular cartridge wall 140, and a self-sealing septum 142 covering a drug outlet 141. The liquid drug is intended to flow through an injection needle 106 attached to the injection device 100 via a needle hub interface 143 when the piston is advanced in the cartridge 104. A cap 115 is mounted at a cap receiving portion 109 in the housing 102, whereby it protects the cartridge 104 and covers the drug outlet 141. An injection button 105 being capable of reciprocating axial motion with respect to the housing 102 is shown in a position where it protrudes from the distal end of the housing 102.

A piston rod 107 is attached to the piston 108 via a piston rod foot 147 and operatively coupled to the injection button 105 such that when the cap 115 is off and the injection button 105 is pressed against the housing 102 the piston rod 107 will advance axially through the housing 102 a certain distance, thereby displacing the piston 108 in the cartridge 104 an equivalent distance to inject a desired amount of drug through the outlet 141.

The movement of the piston rod 107 is realised through a coupling ring 130 being in engagement with a helical track (not visible) in the injection button 105, and a driver 110 which is in engagement with the coupling ring 130 and which is adapted to engage with, and transmit a driving force to, the piston rod 107. The driver 110 is powered by a spring 111 which is a torsionally pre-tensioned compression spring capable of storing and releasing energy for both translational and rotational motion. One end of the spring 111 is retained in a spring base 160, which is both translationally and rotationally fixed relative to the housing 102, and the other end of the spring 111 is in engagement with the driver 110 in such a way that the spring 111 and the driver 110 are able to interchange both forces and torques. The driver 110 is thus capable of performing both translational and rotational motion relative to the housing 102. The spring 111 may for example be torsionally pre-tensioned during assembly of the injection device 100, e.g. by mutually twisting its two end parts a half or a full turn. During dose setting and injection, the movement of the driver 110 is guided by a guide member 120 and a push element 112, which is translationally fixed to the driver 110 via a couple of snap arms 118. The driver 110 comprises two deflectable pawls 176 (only one is visible) which are adapted to engage with a pair of opposed teeth 119 on the piston rod 107 when the driver 110 moves in the distal direction and to ride over the teeth 119 when the driver 110 moves in the proximal direction. In FIG. 3 the pawl 176 is spaced apart from a distal most tooth 191, i.e. the driver 110 is out of engagement with the piston rod 107.

Figure 4:
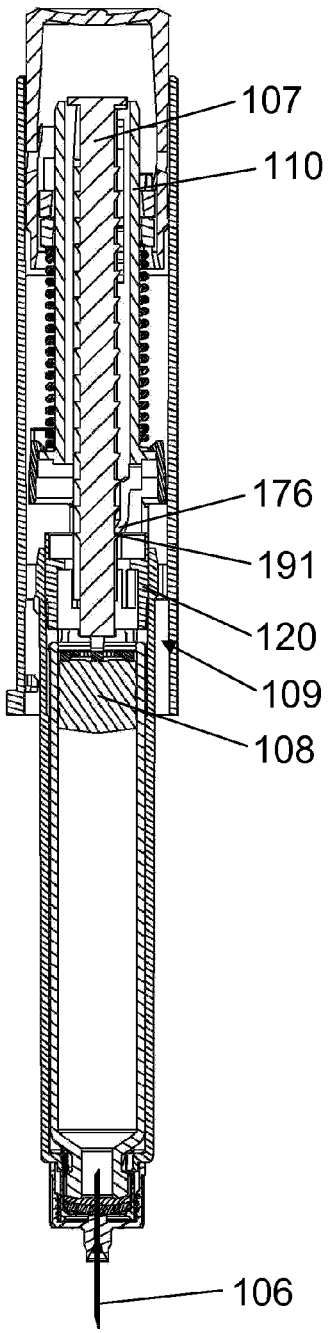
FIG. 4 is a cross sectional view of the injection device of FIG. 3 where the cap has been dismounted and the device is primed.

In FIG. 4 the cap 115 has been removed from the cap receiving portion 109. This has lead to an automatic priming of the injection device 100 by which the pawl 176 is firstly forced distally by the spring 111 into engagement with the distal most tooth 191 and the piston rod 107 is subsequently slaved by the driver 110 to displace the piston 108 a small distance (not visible) in the cartridge 104. The automatic priming sequence will be explained in more detail below.

Figure 5:
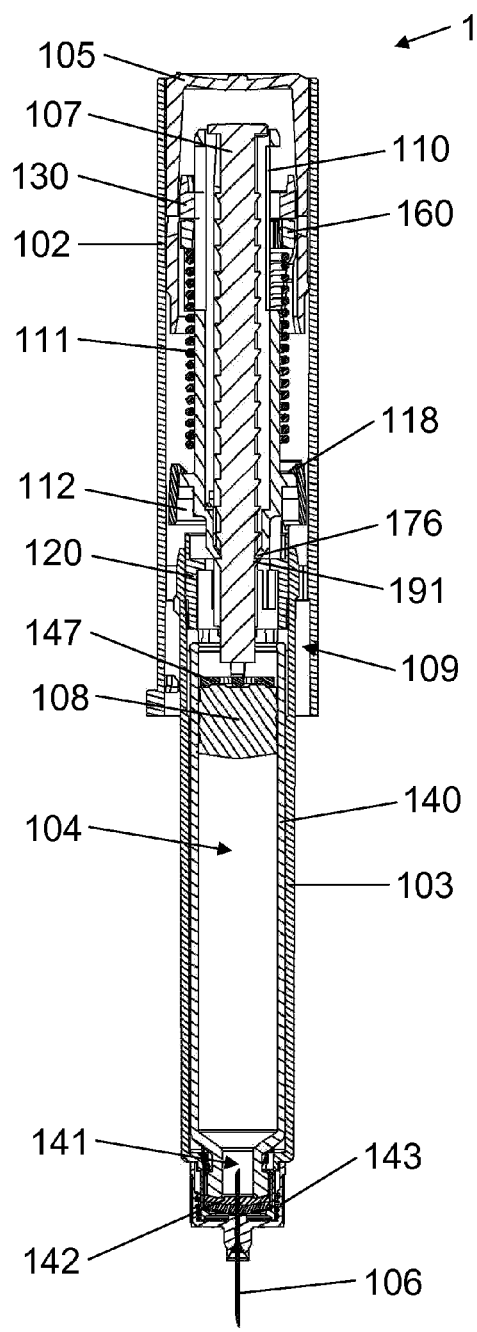
FIG. 5 is a cross sectional view of the injection device of FIG. 3 after the first injection.

FIG. 5 shows the injection device 100 following the first injection. The injection button 105 has been pressed against the housing 102 which has resulted in an activation of the spring 111 and a movement of the piston 108 corresponding to the set dose.

Figure 6:
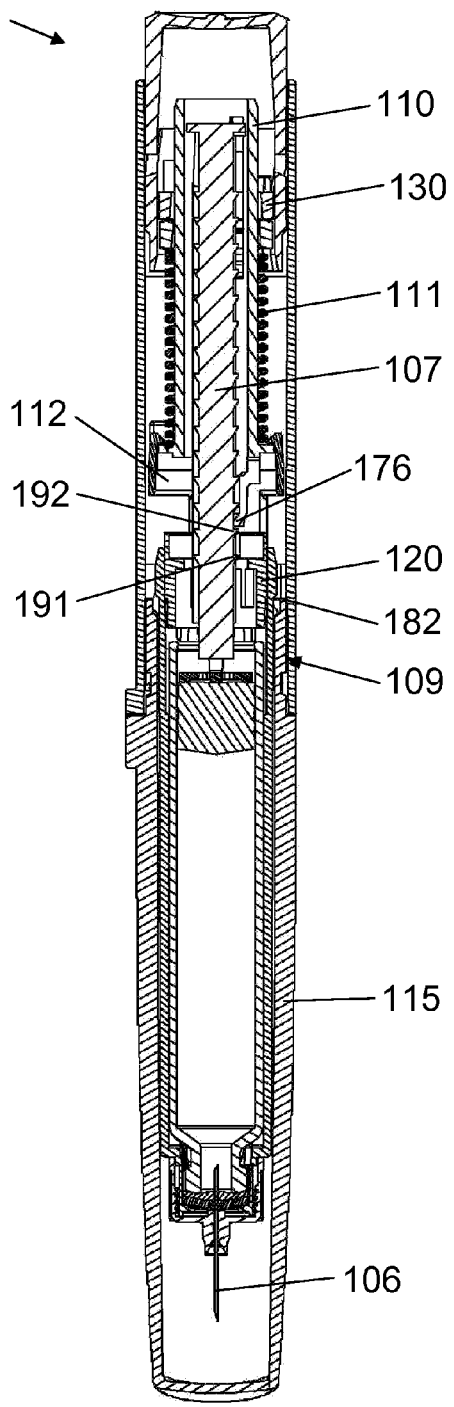
FIG. 6 is a cross sectional view of the injection device of FIG. 3 where the cap has been remounted and the device is loaded.

In FIG. 6 the cap 115 has been remounted on the injection device 100 at the cap receiving portion 109 and a dose has consequently been set. During the remounting the cap 115 abuts the push element 112 and moves the push element 112 proximally.

Thereby the driver 110 is moved proximally and the spring 111 is compressed axially. The pawl 176 is lifted a distance proximally and is now positioned proximally of the next tooth 192 on the piston rod 107, a small clearance being provided between the two.

Figures 7, 8:
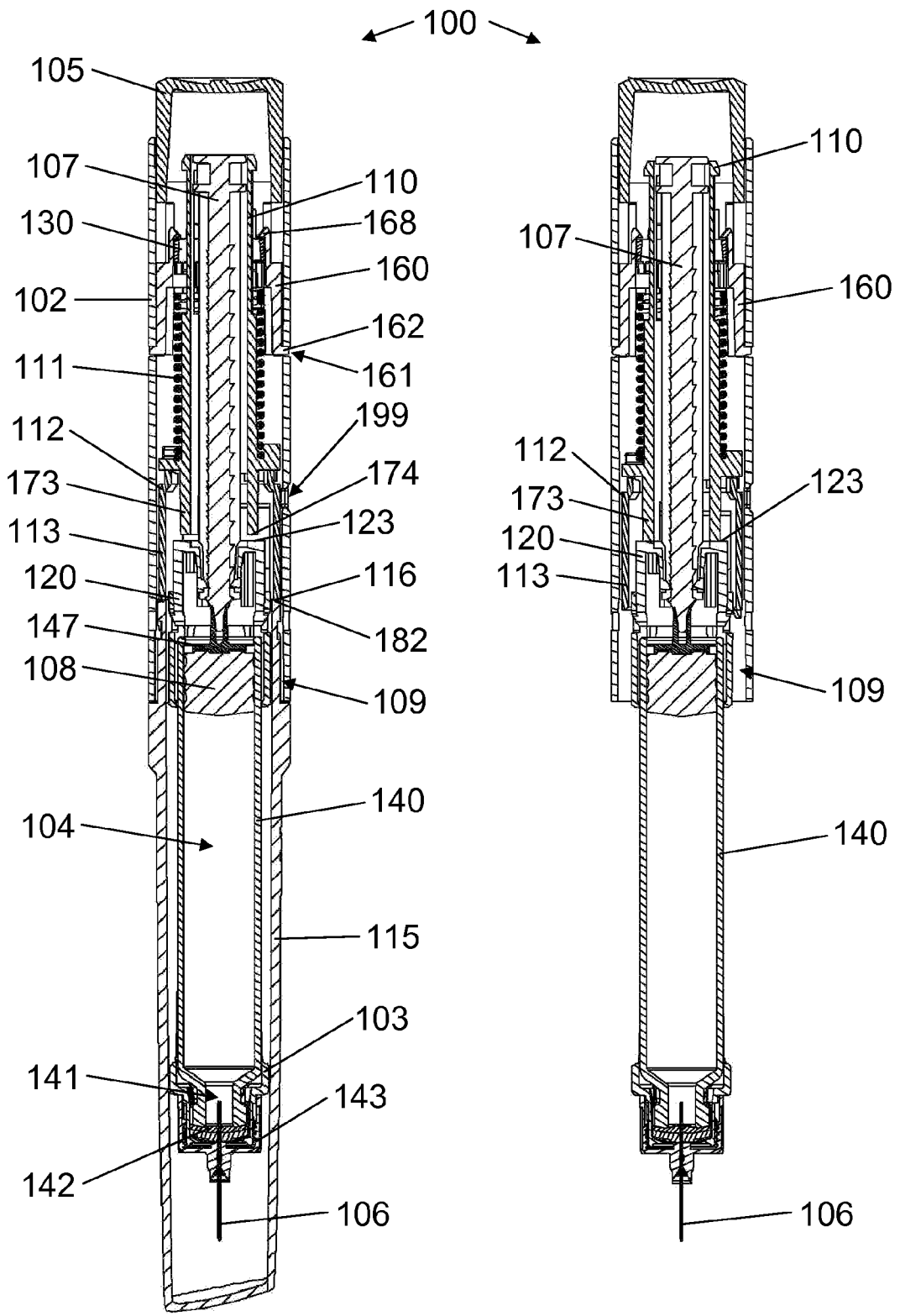
FIG. 7 is another cross sectional view of the injection device of FIG. 3, in a situation corresponding to FIG. 3.
FIG. 8 is another cross sectional view of the injection device of FIG. 3, in a situation corresponding to FIG. 4.

FIG. 7 shows the injection device 100 in a different cross sectional view before the first injection, having the cap 115 mounted at the cap receiving portion 109. The cap 115 is held in the mounted position via a threaded interface (not visible) between the exterior surface of the cap 115 and the interior surface of the housing 102. The cap 115 has a round-going cap edge 182 which is in abutment with a couple of contact soles 116 on the push element 112. The cap edge 182 exerts a force on the contact soles 116 which is transferred via two legs 113 to the driver 110. As the driver 110 is in engagement with the spring 111 the driver 110 is biased by the spring 111 against the push element 112. The push element 112 is thus biased against the cap 115 when the cap 115 is mounted at the cap receiving portion 109.

The driver 110 comprises a couple of slide members 173 which are adapted to control the movements of the driver 110 through an interface with the guide member 120. In FIG. 7 the driver 110 is out of contact with the guide member 120. This is seen by a small clearance between contact soles 174 on the respective slide members 173 and a dose shelf 123 on the guide member 120.

FIG. 7 further shows a see-through window 199 in the housing 102 and apertures 161 which are occupied by hooks 162 providing a rotational and translational fixation of the spring base 160 relative to the housing 102. A couple of snap arms 168 lock the coupling ring 130 translationally to the spring base 160.

FIG. 8 shows the injection device 100 after removal of the cap 115. It is seen that as a consequence of the dismounting of the cap 115 the spring 111 has forced the slide members 173 to move into abutment with the dose shelf 123.

Figure 9:
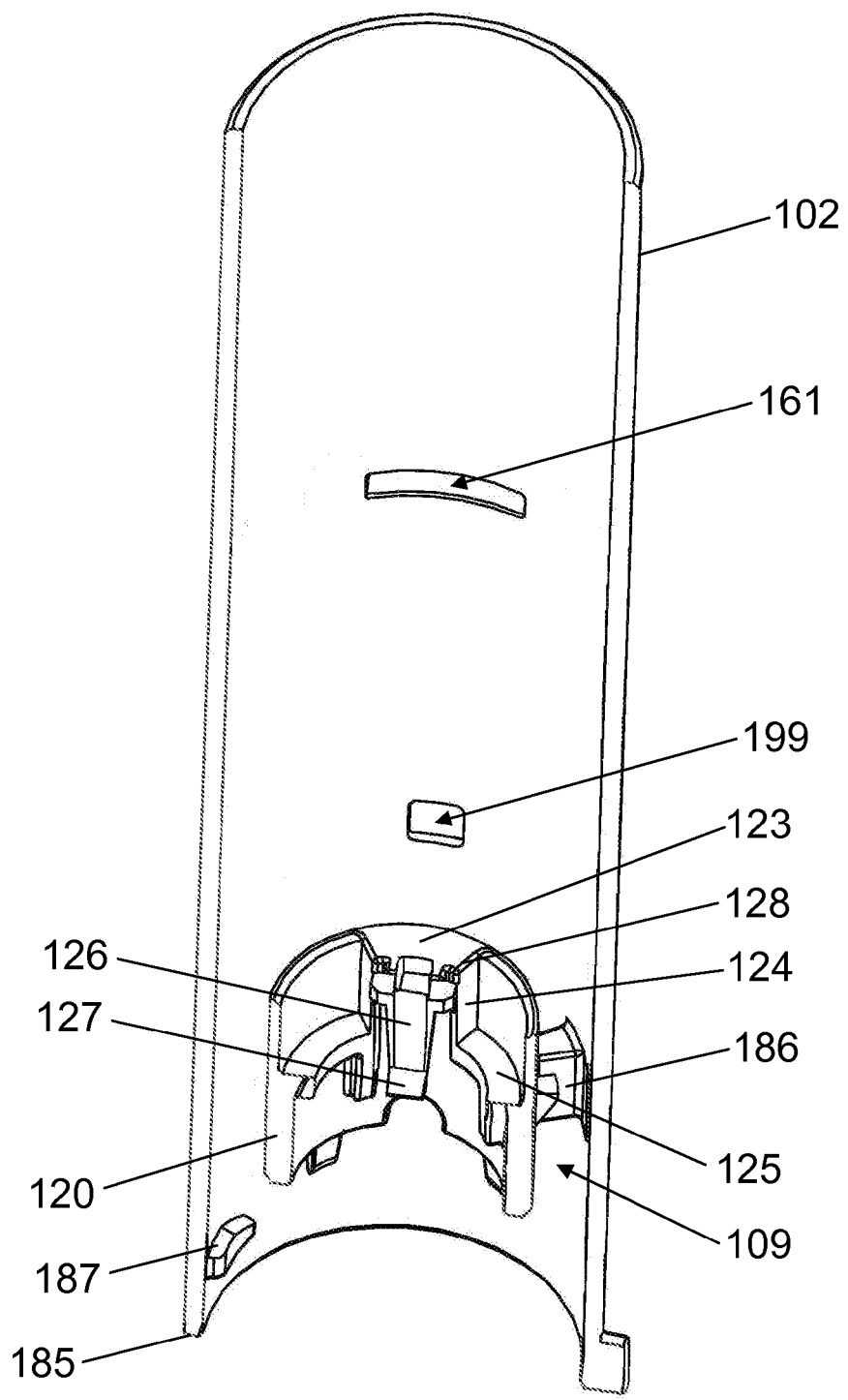
FIG. 9 is a cross sectional perspective view of a housing part, showing a guide member in detail.

FIG. 9 is a cross sectional perspective view of the housing 102, which shows the guide member 120 in more detail. For the sake of clarity the proximal end of the cartridge holding part 103 has been removed from the figure. The guide member 120 comprises the dose shelf 123 adapted to support the driver 110 after removal of the cap 115 from the cap receiving portion 109. A longitudinal guide surface 124 leads from an edge 128 of the dose shelf 123 to an end of dose stop 125. A couple of radially deflectable click fingers 126 are provided on the guide member 120 (only one is visible), each click finger 126 having a tip 127 for engagement with the piston rod 107. The guide member 120 is arranged concentrically in the housing 102 spaced apart from the housing 102 by a number of spacers 186. A protrusion 187 is provided near a distal housing edge 185 for engagement with a helical track segment on the cap 115. This engagement provides for an axial fixation of the cap 115 to the housing 102 when the cap 115 is mounted at the cap receiving portion 109.

Figure 10:
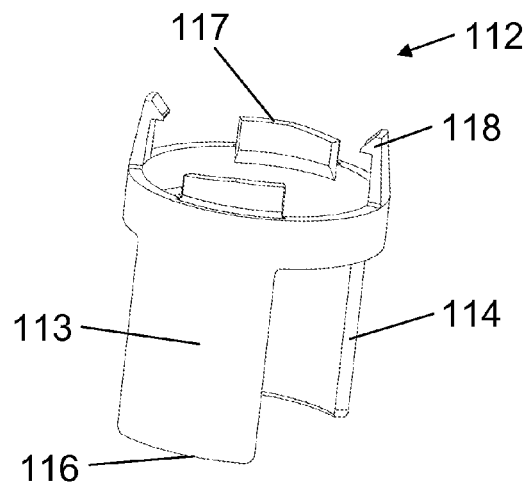
FIG. 10 is a perspective view of a push element used in the injection device of FIG. 3.

FIG. 10 is a perspective view of the push element 112, showing two helical guide segments 117 along which the driver 110 slides during dose setting. The legs 113 are positioned in the housing 102 between respective spacers 186 which thereby provide a rotational fixation of the push element 112 to the housing 102 through contacts with contact surfaces 114. The push element 112 is in this arrangement, however, able to move axially with respect to the housing 102.

Figure 11:
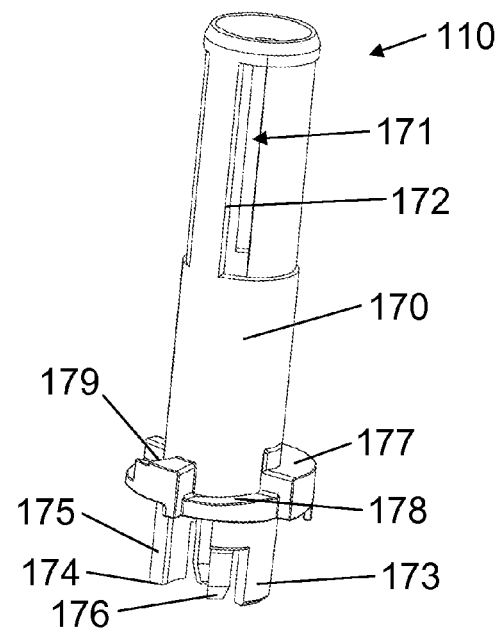
FIG. 11 is a perspective view of a drive member used in the injection device of FIG. 3, FIGS. 12a and 12b are different perspective views of a piston rod used in the injection device of FIG. 3.

FIG. 11 is a perspective view of the drive member 110, generally comprising a tubular body 170 having two radially opposed longitudinal slits 171 extending from its proximal end portion, each slit 171 neighbouring a longitudinal contact surface 172. A shoulder portion 177 connects the tubular body 170 with a distal portion which comprises two slide members 173 adapted to travel the guide surfaces of the guide member 120. The slide members 173 have respective slide surfaces 175 each interfacing with one of the longitudinal guide surfaces 124. The pawls 176 are rigidly connected to the slide members 173 such that the pawls 176 undergo the same translational and/or rotational movement as the slide members 173, and vice versa. The shoulder portion 177 provides a physical interface for the exchange of axial forces between the spring 111 and the driver 110. A spring retaining section 179 provides a physical interface for the exchange of torques between the spring 311 and the driver 310. Helical tracks 178 are adapted to interface with the snap arms 118 on the push element 112 and to enable a rotational motion of the driver 110 with respect to the push element 112.

Figures 12A, 12B:
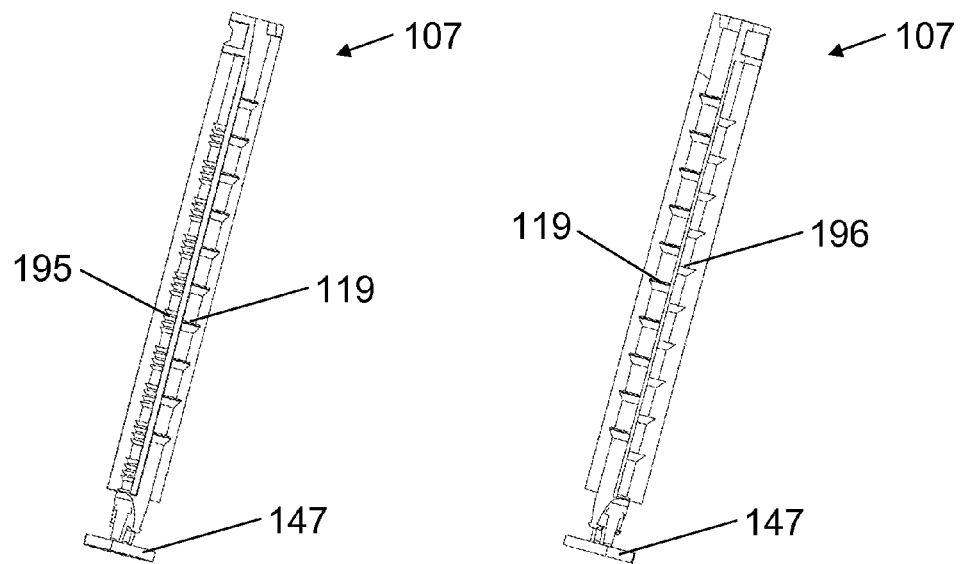

FIG. 12a is a perspective view showing two sides of the piston rod 107. A number of teeth 119 are distributed along the piston rod 107 on the first side, the distance between two consecutive teeth 119 being constant throughout the entire distribution. The teeth 119 are adapted for engagement with the driver 110 during dose injection where the pawl 176 engages a tooth 119 and slaves the piston rod 107 in a forward motion. Further, on the second side, clusters of smaller teeth 195 are evenly distributed along the piston rod 107. During an injection the tip 127 of one of the click fingers 126 rides over the teeth 195 thereby providing an audible confirmation of the progression of the injection.

FIG. 12b is a perspective view showing the other two sides of the piston rod 107. On the third side, opposite to the first side, a number of teeth 119 are distributed in a way similar to the distribution on the first side. On the fourth side a number of teeth 196 are distributed, the teeth 196 being smaller than the teeth 119 but larger than the teeth 195. The distance between two consecutive teeth 196 equals the distance between two consecutive teeth 119 on the first and the third side of the piston rod 107. However, the teeth 196 are axially offset from the teeth 119. At the end of an injection the tip 127 of the other click finger 126 rides over a tooth 196 to provide an audible confirmation of the dose completion. Since the teeth 196 are larger than the teeth 195 the click provided when the click finger 126 overrides a tooth 196 is audibly distinguishable from the click provided when the click finger 126 overrides a tooth 195. The teeth 196 and the click finger tip 127 are arranged so as to provide a unidirectional ratchet and pawl mechanism preventing proximal movement of the piston rod 107 relative to the guide member 120.

Figure 13:
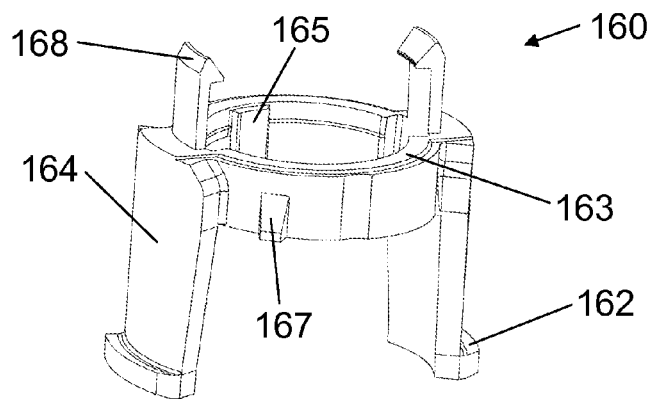
FIG. 13 is a perspective view of a spring holding element used in the injection device of FIG. 3.

FIG. 13 is a perspective view of the spring base 160 which is adapted to hold one end of the spring 111 in a permanent position with respect to the housing 102. The spring base 160 has two radially opposed arms 164 each comprising a hook 162 for engagement with the respective apertures 161 in the housing 102. Due to the engagement between the hooks 162 and the apertures 161 the spring base 160 is completely locked to the housing 102, i.e. the spring base 160 is prevented from performing rotational as well as translatory motion relative to the housing 102. A boss member 165 is provided for retaining the proximal end of the spring 111 and for limiting the axial movements of the driver 110. The spring base 160 further comprises a proximal face 163 adapted to abut with the coupling ring 130, and a pair of snap arms 168 fixing the coupling ring 130 axially with respect to the spring base 160. A projection 167 is also provided for interfacing with the injection button 105.

Figure 14:
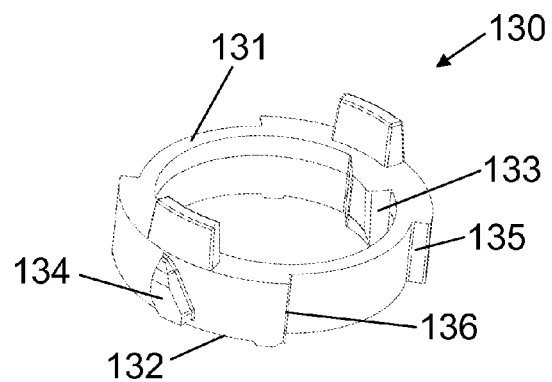
FIG. 14 is a perspective view of a coupling element used in the injection device of FIG. 3.

FIG. 14 is a perspective view of the coupling ring 130 adapted to couple the injection button 105 with the driver 110. The coupling ring 130 has a proximal face 131 and a distal face 132, and two radially opposed protuberances 133 adapted to interact with the contact surfaces 172 on the tubular body 170 of the driver 110 to provide for a rotational master-slave relationship between the coupling ring 130 and the driver 110. During use the protuberances 133 and the contact surfaces 172 are in pair-wise abutment such that when the coupling ring 130 is rotated clockwise the driver 110 is forced to rotate clockwise and when the driver 110 is rotated counter-clockwise the coupling ring 130 is forced to rotate counter-clockwise. The distal face 132 of the coupling ring 130 is adapted to abut with the proximal face 163 of the spring base 160, and the proximal face 131 of the coupling ring 130 is adapted to be engaged by the snap arms 168, i.e. the coupling ring 130 is axially fixed to the spring base 160. The coupling ring 130 and the driver 110 are able to perform relative translatory motion limited by the length of the slits 171. Two protrusions 134 are provided for coupling with the injection button 105. Further, the material thickness of the coupling ring 130 varies circumferentially to provide for a rotational play of the coupling ring 130 in relation to the spring base 160. In that respect, the snap arms 168 will be able to slide between respective walls 135 and 136 when the coupling ring 130 rotates relative to the spring base 160.

Figure 15:
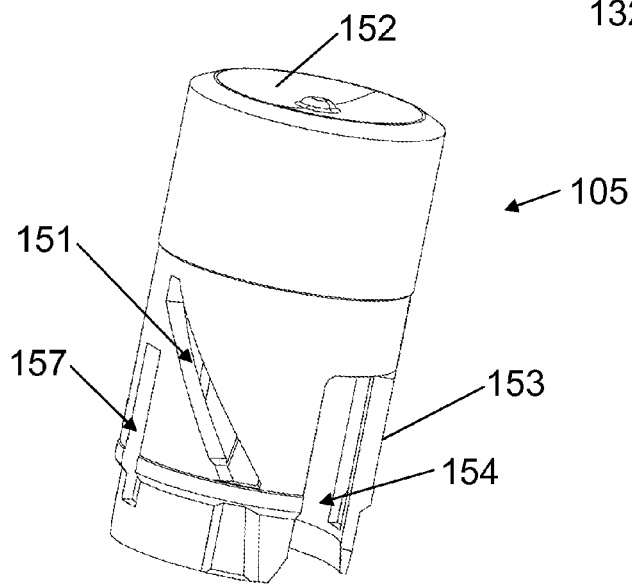
FIG. 15 is a perspective view of an injection button used in the injection device of FIG. 3.

FIG. 15 is a perspective view of the injection button 105 comprising a push face 152 for interfacing with an operator of the injection device 100. The injection button 105 further comprises two flanges 153, each provided with a helical track 151 and a longitudinal slit 157. The helical tracks 151 are adapted to interface with the respective protrusions 134 to transform a translational motion of the injection button 105 to a rotational motion of the coupling ring 130, and vice versa. Further, two clearances 154 are provided for interfacing with the respective arms 164, thereby allowing translational motion of the injection button 105 relative to the spring base 160 while preventing rotational motion of the injection button 105 relative to the spring base 160. As the spring base 160 is rotationally fixed relative to the housing 102 the injection button 105 is only allowed to move translationally with respect to the housing 102. The longitudinal slits 157 are adapted to slidably occupy the respective projections 167. The translational motion of the injection button 105 relative to the spring base 160 is therefore limited in the proximal direction by the interaction between the projections 167 and the respective distal ends of the longitudinal slits 157 and in the distal direction by the interaction between the respective proximal ends of the arms 164 and the respective proximal ends of the clearances 154.

FIG. 16 is a perspective view showing an assembly of the driver 110, the spring 111, the coupling ring 130, the spring base 160, and the piston rod 107. In particular, FIG. 16 shows the axially fixed coupling between the coupling ring 130 and the spring base 160.

FIG. 17 is a perspective view showing an assembly of the injection button 105, the driver 110, the spring 111, the coupling ring 130, the spring base 160, the push element 112, and the piston rod 107, and illustrating the functional connection between the injection button 105 and the driver 110. The figure shows the injection button 105 fully depressed against the spring base 160, i.e. in a position corresponding to a dose having just been injected. The proximal spring end (not visible) is retained in the spring base 160 and the distal spring end is in connection with the driver 110 at the spring retaining section 179. As the spring base 160 is locked to the housing 102 and thereby unable to move the torsionally pre-tensioned spring 111 will bias the driver 110 counter-clockwise, as seen from the injection button 105.

During the injection procedure a push on the push face 152 forces the injection button 105 downwards towards the spring base 160. As the injection button 105 is locked against rotation relative to the spring base 160 this downwards movement is purely translational. During the translational movement of the injection button 105 the protrusions 134 travel the helical tracks 151. This engagement converts the movement of the injection button 105 to a rotational movement of the coupling ring 130, and since the coupling ring 130 is rotationally engaged with the driver 110, the driver 110 will also rotate. The helical tracks 151 are arranged such that when the injection button 105 is pushed towards the spring base 160 the coupling ring 130, and thereby the driver 110, will rotate clockwise, as seen from the injection button 105, i.e. against the rotational bias of the spring 111.

FIG. 18 is a two-dimensional representation of the movement patterns of the respective slide members 173 and the piston rod 107 relative to each other and relative the guide member 120 in the housing 102 during priming, injection and loading of the injection device 100. The representation in FIG. 18 presupposes that the contact soles 174 of the slide members 173 and the pawls 176 are axially aligned with respect to the housing 102. This may not necessarily be the case. However, that specific construction of the driver 110 is adopted here for the sake of clarity. It is understood that the guide member 120 comprises two sets of guiding surfaces which the two slide members 173 travel simultaneously. However, as this movement of the slide members 173 along the respective guiding surfaces is identical only one of them is presented. The various movements will be described in detail below.

Figure 19:
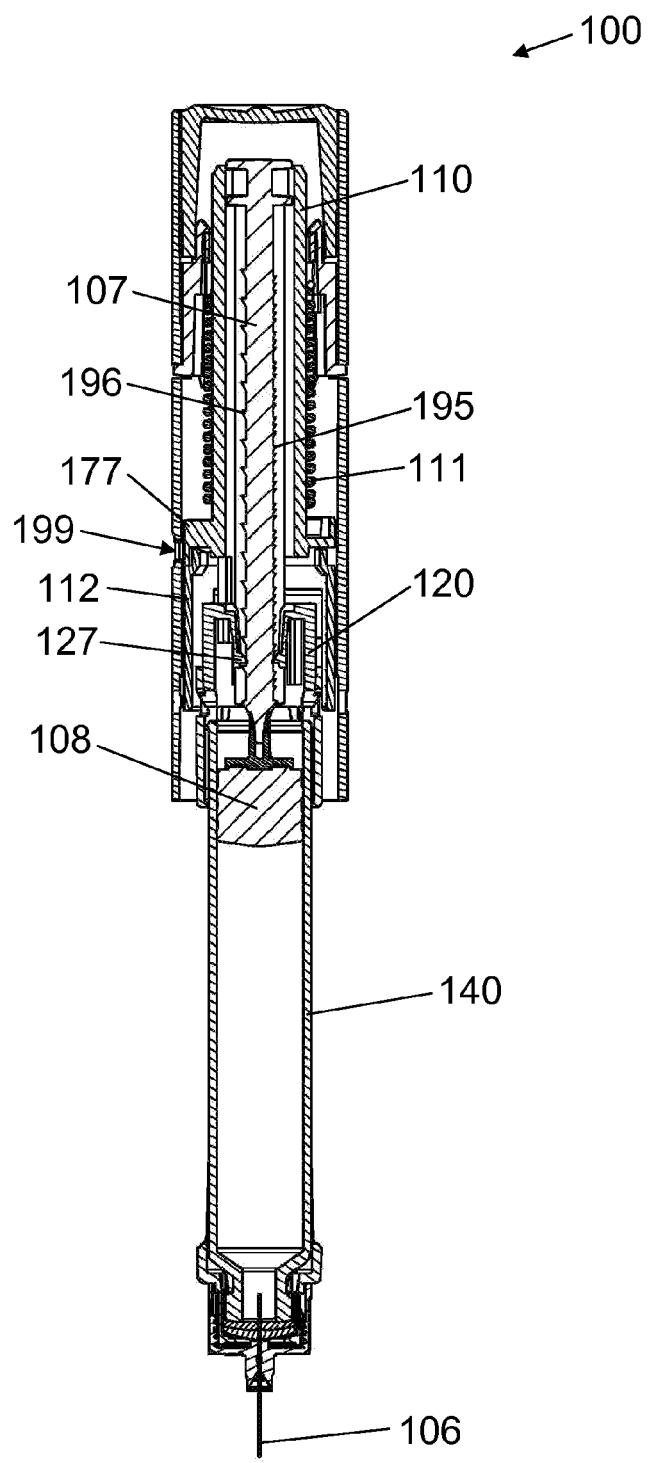
FIG. 19 is a cross sectional view of the injection device of FIG. 3 in an end-of-dose situation, where the drive member is viewable through a window in the housing.

FIG. 19 is a cross sectional view of the injection device 100 following an injection. It is seen that whereas the legs 113 of the push element 112 were visible through the window 199 in FIGS. 7 and 8, the shoulder 177 of the driver 110 is now visible. The interface between the push element 112 and the driver 110 is arranged such that the driver 110 becomes visible through the window 199 only at the point where an injection has been fully completed, i.e. at the point where the entire set dose of drug is expelled from the cartridge 104. The driver 110 has a different colour than the push element 112 so the user is able to check through the window if the desired dose has in fact been delivered. If the window is not completely filled with the colour of the driver 110 a few seconds after the user has pressed down the injection button 105 it is an indication that an obstruction to the delivery has occurred and that the dose is incomplete. In this embodiment the driver 110 is green and the push element 112 is black. However, any combination of colours for the two structural elements can be envisioned, as long as they are visibly distinguishable.

In FIG. 19 it is also seen that the tip 127 of the click finger 126 has just passed an end-of-dose click tooth 196 which has further provided an audible indication of the dose completion. Thereby, two different end-of-dose indicators are provided, a short-lived audible click and a lasting visual colour change, enhancing the safety of the user.

Operation of the Infection Device Represented by FIGS. 3-19

In the following a situation of use of the injection device 100 according to the second embodiment of the invention, as depicted in FIGS. 3-19, will be described.

The injection device 100 shown in FIGS. 3 and 7 is in a non-use state having the cap 115 mounted thereon. As long as the cap 115 is mounted on the injection device 100 at the cap receiving portion 109 it contacts the contact soles 116 of the push element 112 via the cap edge 182 and prevents the push element 112 from moving axially in a distal direction. The push element 112 is in abutment with the driver 110 so the axial position of the push element 112 determines the axial position of the driver 110 in the housing 102. When the cap 115 is mounted at the cap receiving portion 109 the contact soles 174 of the driver 110 are lifted proximally away from the dose shelves 123 of the guide member 120. In this position the cap 115 prevents axial movements of the driver 110 in the distal direction against the bias of the spring 111 which is axially compressed and which exerts a distally directed force on the driver 110. The pawls 176 are spaced apart from the respective teeth 191, resulting in a small clearance between the driver 110 and the piston rod 107.

When the user needs to perform an injection he removes the cap 115 from the injection device 100. If an injection needle 106 is mounted at the needle hub interface 143 the following will happen. The proximally directed force on the push element 112 from the cap 115 is removed and the spring 111 is released and will move the driver 110 in the distal direction until the contact soles 174 of the slide members 173 reach the dose shelves 123. When this happens the driver 110 is brought to a stop and the spring 111 is retained in a new, slightly less compressed state. Due to the rigid construction of the driver 110 the movement of the slide members 173 is reflected directly on the pawls 176 which move a corresponding distance in the distal direction. At some point during this movement the pawls 176 will engage with the pair of teeth 191 and slave the piston rod 107 a small distance. As can be seen from FIG. 18 a removal of the cap 115 from the cap receiving portion 109 results in a distal movement, D, of the slide members 173, and thereby of the driver 110 and the pawls 176. The engagement of the pawls 176 and the teeth 191 (shown as the tooth 192 in FIG. 18 for the sake of clarity) occurs when the driver 110 has moved a distance D−E, and the resulting distal movement of the teeth 191 (the tooth 192 in FIG. 18), and thereby of the piston rod 107, is E.

If there is no initial slack between the piston rod foot 147 and the piston 108 the entire movement of the piston rod 107 will be transferred to the piston 108, i.e. the piston 108 will be displaced the distance E. If there, however, is an initial slack, δ (not shown), between the piston rod foot 147 and the piston 108, then the displacement of the piston 108 will be E−δ.

In any case, a dismounting of the cap 115 from the cap receiving portion 109 will result in an automatic advancement of the piston 108 in the cartridge 104, causing a small volume of the drug to be expelled through the injection needle 106. Having thus automatically de-aerated the injection needle 106 and secured proper abutment between the piston rod foot 147 and the piston 108 the injection device 100 is ready to be used for injection of a dose of the drug.

The user inserts the injection needle 106 through the skin and applies a force to the push face 152 to press the injection button 105 down towards the housing 102. This will result in a purely translatory distal movement of the injection button 105 with respect to the housing 102 until the proximal ends of the arms 164 of the spring base 160 and the proximal ends of the clearances 154 abut. During this movement of the injection button 105 the projections 167 travel the longitudinal slits 157 from a position at the respective distal ends of the longitudinal slits 157 to a position at the respective proximal ends of the longitudinal slits 157. Further, the protrusions 134 travel the helical tracks 151, also in the proximal direction. Since the injection button 105 is rotationally fixed with respect to the housing 102 this movement of the protrusions 134 along the helical tracks 151 will result in a clockwise rotation of the coupling ring 130 with respect to the spring base 160. Due to the rotational master-slave relationship between the coupling ring 130 and the driver 110 the rotation of the coupling ring 130 is directly transferred to the driver 110. Hence, the driver 110 is rotated clockwise against the rotational bias of the spring 111 acting at the spring retaining section 179.

As the driver 110 rotates relative to the housing 102, it also rotates relative to the push element 112 and the guide member 120. The slide members 173 slide along the dose shelves 123 until they reach the edges 128. When the slide members 173 pass the edges 128 the spring 111 is released from its axial retention and forces the driver 110 in the distal direction whereby the slide members 173 travel the longitudinal guide surfaces 124 until they reach the end of dose stops 125. Both during the movement of the slide members 173 along the longitudinal guide surfaces 124 and when the slide members are positioned at the end of dose stops 125 they are biased against the longitudinal guide surfaces 124 due to the torsional tension in the spring 111 biasing the driver 110 in the counter-clockwise direction. This means that when the driver 110 is in the end of dose position it is unable to rotate with respect to the housing 102. Since the driver 110 is unable to rotate with respect to the housing 102, so is the coupling ring 130, and since the coupling ring 130 is unable to rotate with respect to the housing 102 the injection button 105 is forced to maintain its axial position relative to the housing 102. In other words, once the user has activated the injection mechanism the injection button 105 stays depressed against the housing 102.

During the distal movement of the driver 110 the piston rod 107, being slaved by the pawls 176, and thereby the piston 108, is displaced a distance H (see FIG. 18), corresponding to the desired volume of drug to be delivered to the user. The displacement of the piston rod 107 relative to the housing 102 causes one of the click fingers 126 to override a cluster of teeth 195, thereby providing an audible indication to the user that the injection is in fact progressing. In the course of a dose delivery the piston rod 107 is thus displaced a total distance of A, equalling E+H. The piston rod 107, the driver 110, and the guide member 120 are relatively positioned and configured such that E is much smaller than H, i.e. the priming dose is at any time only a fraction of the therapeutic dose.

When the driver 110 moves in the distal direction in the housing 102 it pushes the push element 112 in the same direction. Initially, and as long as the injection is on-going, the push element 112 is visible to the user when he looks through the window 199. However, at exactly the point where the slide members 173 move into abutment with the end of dose stops 125 the driver 110 pushes the push element 112 completely past the window 199, whereby only the driver 110 will be visible to the user when he looks through the window 199. As the driver 110 is green and the push element 112 is black the colour in the window 199 changes when the dose is complete, indicating to the user that the injection has been unobstructed. At the same time the tip 127 of the click finger 126 rides over the end of dose click tooth 196 providing an audible click sound which also indicates to the user that the dose has been carried through.

If an injection needle is not mounted at the needle hub interface 143 when the user removes the cap 115, the driver 110 will be forced in the distal direction by the spring 111 until the pawls 176 engage with the teeth 191 and the piston rod foot 147 is in abutment with the piston 108. Provided there is no initial slack between the piston rod foot 147 and the piston 108 the distal movement of the driver 110 is D−E (see FIG. 18). If there is an initial slack, δ (not shown), between the piston rod foot 147 and the piston 108 then the distal movement of the driver 110 is D−E+δ. In any case the piston rod 107 will exert a pressure on the piston 108 via the piston rod foot 147, but the piston 108 will not move due to the incompressibility of the contents of the cartridge 104. The cartridge 104 remains pressurised, however, due to the spring 111 exerting a constant force on the driver 110, until the user attaches an injection needle 106 to the needle hub interface 143. When the injection needle 106 penetrates the septum 142 the excess pressure in the cartridge 104 is relieved resulting in the spring 111 being able to push the driver 110 further distally until the slide members 173 reach the dose shelves 123. At this point the driver 110 is brought to a stop and the spring 111 is retained in a new, slightly less compressed state. Like in the above described situation this causes the piston 108 to be displaced either a distance E (if there is no initial slack between the piston rod foot 147 and the piston 108) or a distance E−δ (if there is an initial slack between the piston rod foot 147 and the piston 108), leading to a small volume of drug being expelled from the cartridge 104. The injection device 100 has now been automatically primed and a subsequent injection procedure will be identical to the one described in the above.

Remounting of the cap 115 onto the cap receiving portion 109 after an injection will cause a next dose to be set, as explained in the following.

At some point during the remounting of the cap 115 onto the cap receiving portion 109 the cap edge 182 will abut the contact soles 116 of the legs 113, and as the cap edge 182 is moved gradually further towards the proximal end of the injection device 100 the push element 112 will accordingly displace proximally. This proximal displacement of the push element 112 will cause a proximal displacement of the driver 110 against the axial bias of the spring 111. Thereby, the driver 110 is pushed away from the window 199 and the slide members 173 travel the longitudinal guide surfaces 124 from the end of dose stops 125 towards the edges 128. When the slide members 173 have travelled the distance H and reach the edges 128 the rotational bias of the spring 111 will force the driver 110 to rotate counter-clockwise with respect to the housing 102. During this rotation the driver 110 will slide along the helical guide segments 117 on the push element 112. When the driver 110 travels the helical guide segments 117 the pawls 176 are moved a distance D proximally from a position just below the next pair of teeth 192 to a position a little above the teeth 192 in a combined translatory and rotational motion. A small clearance is thereby introduced between the pawls 176 and the teeth 192 (the axial length of the clearance depending on whether or not the loading process has introduced a slack between the piston rod foot 147 and the piston 108).

The counter-clockwise rotation of the driver 110 results in an equal counter-clockwise rotation of the coupling ring 130 due to the engagement between the contact surfaces 172 and the protuberances 133. The rotation of the coupling ring 130 leads to a translatory movement of the injection button 105 in the proximal direction out of the housing 102 due to the interaction between the protrusions 134 and the helical tracks 151. The thereby caused axial movement of the injection button 105 is limited by the travel of the projections 167 in the longitudinal slits 157. When the projections 167 reach the distal ends of the longitudinal slits 157 the movement of the injection button 105 is stopped as the injection button 105 is unable to protrude any further from the housing 102. The rotation of the coupling ring 130 is therefore also stopped, and so is the rotation of the driver 110. The spring 111 is now retained rotationally in the original pre-tensioned state.

The next time the user decides to take an injection he simply dismounts the cap 115 from the cap receiving portion 109 and attaches an injection needle 106 to the needle hub interface 143, whereby the above described automatic priming is performed by the injection device 100. The user does therefore not have to remember to perform a manual priming of the injection device 100 and can go straight to the injection procedure.

The invention claimed is:

1. A medical injection device comprising:
   a variable volume reservoir containing a liquid drug and comprising an outlet and a movable wall,
   an injection mechanism operable to inject a dose of the liquid drug and comprising an actuation member adapted to cause a displacement of the movable wall, a drive member adapted to cause a movement of the actuation member, and bias structure for causing a directional bias of the drive member,
   a removable cap, and
   a cap receiving portion adapted to interface with the cap when the cap is mounted on the injection device so as to cover the outlet,
   wherein the cap receiving portion provides for an operative coupling between the cap and the drive member, the operative coupling comprising the cap abutting or engaging a part associated with the drive member, and
   wherein the drive member is adapted to move from a first position to a second position due to the directional bias of the drive member in response to a relative motion between the cap and the cap receiving portion.

2. An injection device according to claim 1, wherein the relative motion between the cap and the cap receiving portion comprises a relative translatory motion.

3. An injection device according claim 1, wherein the relative motion between the cap and the cap receiving portion comprises a dismounting of the cap from the cap receiving portion.

4. An injection device according to claim 1, further comprising a guide structure adapted to influence the motion of the drive member, wherein the second position is defined by the guide structure when the reservoir is in fluid communication with the surroundings.

5. An injection device according to claim 4, wherein the cap comprises a contact interface for coupling with the injection mechanism and the guide structure comprises a dose shelf for supporting the drive member, and wherein the first position is defined at least partly by the contact interface and the second position is defined by the dose shelf.

6. An injection device according to claim 5, wherein the guide structure further comprises a second plateau for supporting the drive member, and wherein the drive member is displaced from the dose shelf to the end of dose stop when the injection mechanism is operated to inject a dose, the distance between the dose shelf and the end of dose stop corresponding to the volume of drug expelled through the outlet during the injection.

7. An injection device according to claim 6, wherein the actuation member comprises a number of axially spaced apart teeth adapted to be engaged by the drive member, and wherein the distance between two consecutive teeth is greater than the distance between the dose shelf and the end of dose stop.

8. An injection device according to claim 1, further comprising dose setting structure operable to set a dose.

9. An injection device according to claim 8, wherein the dose setting structure is configured to set a predetermined dose when operated.

10. An injection device according to claim 1, wherein the bias structure comprises a spring member adapted to store and release energy for translational and/or rotational motion.

* * * * *